US006258362B1

(12) United States Patent
Loudon et al.

(10) Patent No.: US 6,258,362 B1
(45) Date of Patent: Jul. 10, 2001

(54) STABILIZATION OF HERPES VIRUS PREPARATIONS

(75) Inventors: Peter Thomas Loudon; Claire Alison Varley, both of Cambridge (GB)

(73) Assignee: Cantab Pharmaceuticals Research Ltd, Cambridge (GB)

( * ) Notice: Subject to any disclaimer, the term of this patent is extended or adjusted under 35 U.S.C. 154(b) by 0 days.

(21) Appl. No.: 09/300,073

(22) Filed: Apr. 26, 1999

Related U.S. Application Data

(60) Provisional application No. 60/083,402, filed on Apr. 29, 1998.

(30) Foreign Application Priority Data

Apr. 24, 1998 (GB) .................................................. 9808922

(51) Int. Cl.[7] .......................... A61K 39/245; G01N 1/30
(52) U.S. Cl. ..................................... 424/229.1; 424/230.1; 424/280.1; 435/5; 435/14; 435/40.5
(58) Field of Search ............................. 424/229.1, 230.1, 424/280.1; 435/3, 5, 14; 34/40.5, 284

(56) References Cited

U.S. PATENT DOCUMENTS

| | | | |
|---|---|---|---|
| 3,915,794 | * | 10/1975 | Zygraich et al. . |
| 3,985,615 | * | 10/1976 | Kubo . |
| 4,147,772 | * | 4/1979 | McAleer et al. . |
| 4,338,335 | * | 7/1982 | McAleer et al. . |
| 4,500,512 | * | 2/1985 | Barme . |
| 4,622,222 | * | 11/1986 | Horváth et al. . |
| 4,985,244 | * | 1/1991 | Makino et al. . |
| 5,024,836 | * | 6/1991 | McAleer et al. . |
| 5,075,110 | * | 12/1991 | Francon et al. . |
| 5,360,736 | * | 11/1994 | Provost et al. . |
| 5,607,852 | * | 3/1997 | Provost et al. . |
| 5,650,153 | * | 7/1997 | Ishikawa et al. .................. 424/229.1 |
| 5,665,362 | * | 9/1997 | Inglis et al. . |
| 5,792,643 | * | 8/1998 | Herrmann et al. . |
| 5,837,261 | * | 11/1998 | Inglis et al. . |

FOREIGN PATENT DOCUMENTS

| | | | |
|---|---|---|---|
| 209738 | | 5/1984 | (DE) . |
| 0008255 | * | 7/1979 | (EP) . |
| 0028563 | * | 10/1980 | (EP) . |
| 0048194 | * | 8/1981 | (EP) . |
| 0252059 | | 6/1987 | (EP) . |
| 0290197 | | 4/1988 | (EP) . |
| 0295043 | | 6/1988 | (EP) . |
| 0353108 | | 6/1989 | (EP) . |
| 0573107 | | 5/1993 | (EP) . |
| 63230851 | * | 12/1990 | (JP) . |
| 06234659 | | 8/1994 | (JP) . |
| WO 92/05263 | | 4/1992 | (WO) . |
| WO 93/18790 | | 9/1993 | (WO) . |
| WO 94/21807 | | 9/1994 | (WO) . |
| WO 95/10601 | | 4/1995 | (WO) . |
| WO 96/29096 | | 9/1996 | (WO) . |
| WO 98/28000 | | 7/1998 | (WO) . |

OTHER PUBLICATIONS

Potgieter et al. Onderstepoort J Vet Res, 1982, vol. 48 (3), 179–180.*

Samorek–Salamonowicz et al. Medycyna Weterynaryjna, 1993, vol. 49, 162–163.*

* cited by examiner

Primary Examiner—Ali R. Salimi
(74) Attorney, Agent, or Firm—Klarquist Sparkman Campbell Leigh & Whinston, LLP

(57) ABSTRACT

Stabilized dried pharmaceutical compositions dispersible in aqueous liquid or injection comprise (i) virus e.g. for use as a vaccine or vector, preferably a herpesvirus, e.g. attenuated or genetically disabled infectious herpes simplex virus or varicella zoster virus, (ii) polysaccharide, e.g. dextran, and/or a source of mixed aminoacids of vegetable or bacterial origin, (iii) a buffer, and (iv) a mono- or oligo-saccharide or derivative thereof.

19 Claims, No Drawings

STABILIZATION OF HERPES VIRUS PREPARATIONS

PRIORITY CLAIM

This application claims priority from co-pending U.S. provisional application Ser. No. 60/083,402, filed Apr. 29, 1998, which is herein incorporated by reference.

FIELD OF THE INVENTION

This invention relates to preparations of viruses, e.g. for vaccine or other pharmaceutical or research use, to their stabilisation, and to processes of producing such preparations, as well as to their use, e.g. as vaccines or as virus vectors.

BACKGROUND OF THE INVENTION AND PRIOR ART

It is known to freeze and/or lyophilise viable virus preparations for laboratory or vaccine use in order to preserve their activity.

Numerous methods are known for producing live virus preparations, e.g. herpesvirus preparations, for vaccine and other purposes.

U.S. Pat. No. 5,024,836 (Jun. 18, 1991) (Merck & Co Inc: W J McAleer et al) describes a stable lyophilized live herpes virus vaccine that comprises from about 0.5% to about 8% moisture, and claims a gas injected lyophilized live attenuated varicella virus vaccine which comprises 2% to 8% moisture.

U.S. Pat. No. 5,075,110 (Dec. 24, 1991) and EP 0353108 (Institut Merieux: A J Francon et al) describe stabilization of attenuated lyophilized vaccines with amide or thioamide lyophilization excipients, e.g. urea.

EP 0048194 (Merck & Co Inc.: M R Hillemanet al) describes lyophilization processes in which lyophilization time and expense are reduced by shell freezing liquid vaccine prior to lyophilization by rotating the vial on its side in a liquid bath maintained at a temperature below the eutectic point of the vaccine.

U.S. Pat. No. 4,338,335 (Jul. 06, 1982) and EP 0028563 (Merck & Co Inc: W J McAleer et al) describe stabilizer for liquid vaccines, and stabilized liquid live viral vaccine containing live virus, partially hydrolyzed gelatin, a monosaccharide or disaccharide, a cell culture medium, L-glutamic acid, L-arginine and buffer to maintain pH at from about 6.0 to about 6.5.

EP 0008255 (Merck & Co. Inc.: W J McAleer et al) describes herpes virus vaccine and its preparation, especially Marek's Disease vaccine. The virus is lyophilized in the presence of a pH controlled buffered stabilizer, so that the vaccine can be reconstituted with distilled water.

EP 0295043 (Dec. 14, 1988) (Kitasato Institute: S Makino et al) describes stabilized live attenuated vaccine comprising at least one live attenuated plain virus selected from measles, mumps or rubella virus and, as a stabilizing agent, lactose, saccharose, D-sorbitol, sodium glutamate and gelatin hydrolysate.

EP 0252059 (Smithkline Biologicals S.A.: E D'Hondt) describes stabilizers for attenuated vaccines, containing lactose, sorbitol, dextran, casein hydrolysate, L-glutamate, EDTA and buffer at a pH 6.7–7.2.

WO 96/29096 (Hisamitsu Pharmaceutical Co., Inc.: H Kuma et al) describes production of gene transfer preparations by freeze-drying a mixture of a recombinant virus vector with at least one additive selected among arginine, glutamic acid (or sodium salt thereof), serine, glucose, inositol, lactose, mannitol, sorbitol, trehalose and xylose.

U.S. Pat. No. 4,985,244 (Jan. 15, 1991) (Kitasato Institute: S Makino et al) describes stabilized live attenuated vaccine with improved thermal stability, which comprises live attenuated plain measles, mumps or rubella virus vaccine grown in a medium-199 for cell culture, or a combined live attenuated vaccine, stabilized with lactose, saccharose, D-sorbitol, sodium glutamate and gelatin hydrolyzate.

U.S. Pat. No. 4,622,222 (Nov. 11, 1986) (Phylaxia Oltoanyagtermelo Vallalat: E Horvth et al) describes lyophilized vaccine against duck virus hepatitis using attenuated virus, and its production using infected duck embryos, including lyophilising the sterile virus material with collidone, gelatin, glucose and sucrose.

U.S. Pat. No. 4,500,512 (Feb. 19, 1985) (Institut Pasteur:, M Barme) describes stabilized vaccines containing live viruses, especially for yellow fever virus, and stabilizers comprising phosphate buffer, calcium and magnesium ions, lactose, sorbitol and amino acid selected from histidine, alanine, valine, threonine, arginine, methionine, hydroxyproline, lysine, isoleucine, phenylalanine, serine, preferably histidine and alanine. The stabilized vaccine is lyophilized.

U.S. Pat. No. 3,985,615 (Osaka Res Foundation: T Kubo et al) describes production of live attenuated varicella virus for vaccine use by culture comprising passage in guinea pig primary embryonic tissue cells. U.S. Pat. No. 5,024,836 (Merck: W J McAleer et al) relates to production of lyophilized vaccine preparations based thereon.

U.S. Pat. No. 5,792,643 (Mar. 28, 1997) and WO 95/10601 (Viagene: S M Hermann et al) disclose preservation of infectious recombinant viruses using a saccharide, high molecular weight structural additive, a buffer and water, and cooling the mixture to below the eutectic or glass transition point, and removing water by sublimation to less than 10% water content.

WO 93/18790 (L K Csatary) describes lyophilised viral vaccines (e.g. MDV vaccines) with modified starch such as hydroxyethyl starch mw 100,000–300,000 added as protective colloid prior to lyophilisation.

JP06234659 (Aug. 23, 1994) (Z H Handai Biseibutsubyo Kenkyukai) discloses stabilised live vaccine containing attenuated or recombinant live varicella virus and a stabiliser free from Ca2+ion and Mg2+ion, preferably with gelatin or gelatin hydrolysate or a chelating agent such as EDTA.

EP 0290197 (Nov. 09, 1988) (Merck & Co Inc: R Z Maigetter wet al) discloses stable gas injected lyophilised live herpes virus vaccine comprising 0.5–8% moisture permitting storage at standard refrigerator conditions, i.e. 5 deg. C., rather than freezer conditions (−20 deg. C.). Gas injection during the primary cycle of the lyophilisation process and drying to higher moisture levels reduces the lyophilisation time, typically to 7–11 hrs for combined primary and secondary cycles.

DD-209738 (Cent Cerc Bioprep: I V Patrascu) illustrates production of of herpesvirus vaccine against Marek's disease by (a) culturing embryo cells on dextran microspheres; (b) inoculating the culture at 80% confluence with turkey herpes virus strain FC-126; (c) collecting the infected cells in SPGA medium (sucrose, phosphate, glutamate, bovine albumin fraction V) when the cytopathic effect is 80%; (d) ultrasonic pulsing and centrifugation to recover a first crop of vaccine; (e) resuspending the sediment in SPGA medium and repeating step (d) to obtain a second crop of vaccine (to increase vaccine yield); (f) freezing the combined vaccines at −100 deg. C. prior to determining the virus titre; and (g) diluting with SPGA medium and freeze drying.

JP06234659-A (Z H Handai Biseibutsubyo Kenkyukai) describes, in an example, production of herpesviral vaccine on human diploid fibroblast MRC-5 cells cultured in MEM medium at 37 deg. C.; comprising inoculation of varicella virus Oka strain seed virus at a MOI of 0.03 to MRC-5 cells and culture at 37 deg. C. for 2 days. Virus is then suspended in a solution containing NaCl, KCl, Na2HPO4, KH2PO4, sucrose, L-glutamate, gelatin, gelatin hydrolysate and EDA-3Na.

EP 0 573 107, U.S. Pat. No. 5,360,736 and U.S. Pat. No. 5,607,852 (Merck: P A Friedman et al) describe processes for production of attenuated varicella zoster virus vaccine.

WO 98/28000 (Merck & Co., Inc., Rahway, N.J., U.S.: D B Volkin et al.) describes vaccine formulations (e.g. measles, mumps, rubella, VZV or herpes simplex) comprising 6-carbon polyhydric alcohol, disaccharide and buffer.

U.S. Pat. No. 3,915,794 (Recherche et Industrie Therapeutique, Belgium: Z Nathan and J Petermans) describes stable virus preparations comprising group B herpes virus (e.g. turkey hepersvirus) and a buffered aqueous solution pH 6.5–7.5 comprising polyvinylpyrrolidone, sugar, glutamate and chelating agent.

U.S. Pat. No. 4,147,772 (Apr. 03, 1979) (Merck & Co. Inc: W J McAleer et al) describes a lyophilised vaccine with pH between about 6.0 and 6.5 and comprising live virus, partially hydrolysed gelatin (M.Wt. about 3,000), a 6-carbon polyhydric alcohol, cell culture medium and acidic buffer.

U.S. Pat. No. 5,665,362 and WO 92/05263 (Cantab Pharmaceuticals Research Ltd: S C Inglis et al) and U.S. Pat. No. 5,837,261 and WO 94/21807 (Cantab Pharmaceuticals Research: Inglis et al) and documents cited therein illustrate prior knowledge related to genetically disabled infectious herpesvirus such as herpes simplex virus, e.g. for vaccine purposes and of providing recombinant cells and culture methods for producing them. Other disclosures of genetically disabled herpesvirus and cells for producing them are also included in the prior art, e.g. certain references noted below.

It remains desirable to provide further forms of stabilised virus preparations, e.g. for vaccine use.

The Present Invention

According to the present invention there is provided a stabilised dried pharmaceutical composition comprising a virus, which is dispersible in aqueous liquid for injection and comprises: virus e.g. as active vaccine component, e.g. a herpesvirus; vegetable peptone; buffer; and saccharide or sugar alcohol, or other mono- or oligo-saccharide or derivative thereof, e.g. lactose or sorbitol. The composition can optionally also contain dextran or other polysaccharide with a molecular weight above about 5000, which can if desired substitute for the vegetable peptone. Optional further ingredients can include further aminoacid, e.g. diacidic aminoacid such as sodium L-glutamate or L-aspartate, or a mixture of aminoacids. Among further ingedients that can be suitable are those referred to in the prior art documents mentioned above, very preferably those of vegetable or mineral origin.

In certain examples, the stabilised dried pharmaceutical compositions can comprise (i) infectious virus as active component, e.g. for use as a vaccine or as a virus vector, e.g. for gene therapy, preferably a herpesvirus, e.g. an attenuated or genetically disabled infectious herpes virus such as HSV or varicella zoster virus, (ii) polysaccharide with a molecular weight above about 5000, preferably about 11,000 to about 40,000, and less than 70,000 e.g. dextran, and/or a source of mixed aminoacids of vegetable or bacterial origin, e.g. vegetable peptone, e.g. peptone made by enzymic hydrolysis of soybean protein (iii) buffer, e.g. tris-HCl, bicarbonate, phosphate and/or citrate, and (iv) saccharide or sugar alcohol, e.g. lactose, sucrose or sorbitol. Certain examples can contain one but not both of the polysaccharide components mentioned above and the source of mixed amino acids. In addition to the components mentioned above the composition can contain additional ingredients, which can include further aminoacid, e.g. diacidic aminoacid such as sodium L-glutamate or L-aspartate, or a mixture of aminoacids. Examples of additional ingredients that can be suitable components of compositions of the invention are those referred to in the prior art documents mentioned above, very preferably ingredients of vegetable or mineral origin.

Compositions of the invention include examples free from protein (other than any protein forming part of the active vaccine component), in particular free from gelatin or other animal protein or its hydrolysate or other material of animal origin. Where the compositions include a source of mixed aminoacids, such as vegetable peptone, they can be free of materials with molecular weight above about 2000, e.g. free of materials of m.w. above about 1500 (other than any materials forming part of the active vaccine component).

It has been found that lyophilised compositions as described herein can have good retention of titre at the end of useful storage periods at moderate temperatures, e.g. above 0 deg. C., e.g. at about 8 deg. C., after lyophilisation of the composition. In certain test conditions, without limitation, the dried compositions retained at 16 weeks, or at 52 weeks, at 8 deg. C. an infectious virus titre within 0.5 of a log of the titre found immediately after lyophilisation, e.g. at titres in the range $10^5$ to $10^6$ pfu/ml relative to the liquid volume before lyophilisation.

A further aspect of the invention concerns the use of vegetable peptone or other mixed amino acids of vegetable or bacterial origin, free of animal protein or animal protein hydrolysate, or other material of animal origin, in compositions for stabilising virus, and in the manufacture of dried stabilised virus compositions for vaccine and other uses as mentioned herein.

Vegetable peptone suitable and presently preferred for making compositions according to the invention can for example consist essentially of a preparation made from clean edible solvent-extracted soya flour by hydrolytic digestion with protease, to give a product with an average molecular weight in the range about 300–400 and substantially free from higher m.w. constituents above about m.w. 2000. Soluble carbohydrate of vegetable origin can also be present in such a peptone preparation. Alternatively, mixed aminoacids of vegetable or bacterial origin can be used in place of peptone as described above.

Compositions acording to the invention can generally be made in accordance with per-se known pharmaceutical practice so that they reach acceptable standards e.g. of sterility.

The total content of components in the dried preparation can be such that upon reconstitution with sterile liquid for injection, e.g. water for injection or saline for injection, the composition can be used to provide an injection which is an acceptable approximation to isotonic concentration. An exactly isotonic concentration provides about 330 mOsm, and in accordance with existing practice it can be an acceptable approximation to achieve this e.g. within the range of about 100–600 mOsm, generally within about 250–450 mOsm. 'Isotonic' herein normally refers to such an approximation.

The dose of virus in a lyophilised preparation according to an example of the invention can be chosen to be such as to yield, in the reconstituted liquid for injection, a dose of for example about $10^3$ to about $10^8$ pfu virus. A commonly chosen example of a volume of a dose for injection is about 0.5 ml.

The lyophilised preparation can be prepared from a liquid composition which is either of the same concentration in its principal components as the liquid to be reconstituted, or of greater or lesser concentration.

The moisture content of the lyophilised product can range from 0.5–15% and can be below about 10%, e.g. below about 5%, e.g. down to about 2% or less.

Also provided by the invention is a process for producing a stabilised dried pharmaceutical preparation of a herpesvirus vaccine, which is dispersible in aqueous liquid for injection, and which comprises lyophilising a sterile aqueous composition containing (i) virus as active vaccine component, preferably a herpesvirus, e.g. an attenuated or genetically disabled infectious herpes simplex virus or varicella zoster virus, (ii) vegetable peptone as mentioned above, (iii) buffer, e.g. tris-HCl, phosphate and/or citrate, and (iv) saccharide or sugar alcohol, e.g. lactose or sorbitol. The composition can optionally also contain (v) dextran or other polysaccharide e.g. with m.w. above about 5000, which can if desired substitute for the vegetable peptone.

The lyophilisation of the product can be carried out over any suitable period according to conventional lyophilisation practice, e.g. at a temperature below the glass transition temperature of the frozen liquid to be lyophilised, and the product can be in the form of a solid dried cake within a glass vial, perferably under sterile conditions. The freeze-drying process can comprise per-se known process steps to achieve two-stage drying in which a first stage of sublimation of the water content takes place at a temperature of for example about –40 deg. C. or lower, and then the temperature of the composition is raised to a higher temperature, e.g. 0 to +10 deg. C., when the drying has proceeded enough for the cake formed by the partially dried composition to retain its shape at the higher temperature, and a further amount of water is removed during and after such raising of temperature, still at reduced pressure. In practice it has been found that reduction of water content down to the range about 2 to about 9% by weight is conveniently achievable and satisfactory for product stability.

The product can be rehydrated at convenience with sterile aqueous liquid, e.g. water for injection.

Also provided according to the invention is a process for producing a liquid preparation of a virus vaccine for injection, which comprises dispersing or dissolving a sterile lyophilised preparation as specified above, e.g. a stabilised dried pharmaceutical preparation of a recombinant herpes simplex virus, in aqueous liquid for injection so as to produce a liquid composition of approximately isotonic concentration.

Examples of the present invention are stabilised dried preparations of active herpesvirus, dried from liquid aqueous preparations containing stabilising agents as follows (w/v): disaccharide 2–12%, e.g. sucrose, lactose, and/or trehalose, preferably at least two disaccharides each at least at 2%; optionally monosaccharide or monosaccharide sugar alcohol e.g. sorbitol at 1.5–4%; optionally dextran at 1–5%; optionally sodium glutamate or aspartate at 0.05–0.7%; and vegetable peptone at 1–4%.

The compositions can also comprise other materials such as other colloids, which where present are preferably polysaccharides or polysaccharide derivatives such as hydroxyethyl starch.

The virus of the formulations can generally comprise live virus, preferably attenuated or genetically disabled.

The virus is preferably an infectious virus, e.g. a herpesvirus, and can be a genetically disabled virus of e.g. of one of the kinds described or referred to in WO 92/05263 (Immunology Ltd: Inglis et al); L H Nguyen, D Knipe et al, J Virol 66(12) (December 1992) 7067–7072; WO 94/01573 (Akzo: Peeters et al:) WO 94/03595 (Akzo: Visser et al:) WO 94/21807 (Cantab Pharmaceuticals Research Ltd: Inglis et al); WO 95/18852 (Harvard College and Dana-Farber Cancer Institute: D Knipe, et al); WO 96/04395 (Lynxvale Ltd: P Speck); and WO 96/26267 (Cantab Pharmaceuticals Research Ltd: MEG Boursnell et al).

The invention is particularly applicable for example to herpesviruses and poxviruses among others. Particularly useful applications are for the stabilisation of HSV, e.g. HSV-2, e.g. in the form of disabled HSV-2 such as that described in WO 94/21807 (Cantab Pharmaceuticals: Inglis et al), and WO 96/26267 (Cantab Pharmaceuticals Research Ltd: MEG Boursnell et al), e.g. in embodiments wherein the virus carries exogenous genetic material encoding an immunomodulator or a heterologous antigen. Other herpesviruses such as for example VZV, BHV, and PRV can also be formulated as described herein.

Examples of compositions of the invention can for example comprise immunogens and vaccines and viral vector preparations for in-vivo and ex-vivo use. The compositions can comprise immunogens other than the virus described above, e.g. immunomodulators such as interleukins, e.g. IL-12; and per-se known stabilisers and excipients such as may be desired for purposes of a given application in hand.

A composition such as described herein can be passed through a sterilising filter before the drying step and can be sterile (apart from possessing any desired and intended biological activity such as that of the virus itself).

Examples of the compositions provided hereby can be made free of constituent materials of bovine origin, and in some cases of other (or any) animal origin.

Compositions provided hereby can have useful stability, e.g. in regard to the proportion of infectious virus which survives the lyophilisation process, and/or in regard to the storage stability over extended periods of time of the product of lyophilisation, e.g. during storage at temperatures in the range about 4–10 deg. C., e.g. about 8 deg. C.

The invention is illustrated by the following examples given without intent to limit the scope of the invention.

EXAMPLE 1

A liquid preparation of genetically disabled herpes simplex virus type 2 HSV-2 (for which see specification WO 94/21807, but the invention is also applicable to other viruses) can be lyophilised acording to an example of the present invention by dispersing the virus in aqueous liquid of the following composition (w/v in aq:): 5% lactose, 5% sucrose, 1.8% sorbitol, 0.1% sodium glutamate, 2% vegetable peptone, buffer pH 5.5-pH 8, preferably about pH 7 (about 50 to 100 mM Tris-HCl, about 10 mM sodium citrate with additional sodium chloride, e.g. up to about 138 mM, or 10 mM sodium and potassium phosphate), and lyophilising the product in per-se known manner in standard glass vials.

In variants of this example the lactose can be substituted by sucrose or trehalose, or omitted.

At the end of a storage period of about 16 weeks=at 8 deg. C. certain specimens made according to this example and in which phosphate buffer is present had a titre in pfu/ml (of original liquid volume before lyophilisation) within 0.5 of a log of the titre found immediately after lyophilisation and had a titre of the order of $10^5$ to $10^6$ pfu/ml relative to the liquid volume before lyophilization.

In a variant of this example Tris buffer can be used in place of phosphate buffer.

EXAMPLE 2

A lyophilised preparation of the genetically disabled HSV-2 of the preceding example can be made as in the preceding example except that the liquid before lyophilisation comprises, besides virus: 2.5% dextran (m.w. about 11,000 to 40,000 or more, preferably about 11,000), 0.5% sodium glutamate, 2.5% sucrose, and buffer pH 5.5-pH 8, preferably about pH 7, as described for Example 1.

In a version of this example the buffer comprises M-199 tissue culture medium, and at the end of a storage period of about 52 weeks=at 8 deg. C. certain specimens made according to this example had a titre in pfu/ml (of original liquid volume before lyophilisation) within 0.5 of a log of the titre immediately after lyophilisation, and had a titre of the order of $10^5$ to $10^6$ pfu/ml relative to the liquid volume before lyophilization.

In variants of this example sucrose can be replaced by trehalose.

At the end of a storage period of about 54 weeks=at 8 deg. C. certain specimens made according to this example and in which trehalose is present had a titre in pfu/ml (of original liquid volume before lyophilisation) within 0.5 of a log of the titre found immediately after lyophilisation.

EXAMPLE 3

A lyophilised preparation of genetically disabled HSV-2 as in example 1 can be made as in example 1, using components as in example 2 except that the dextran component is dextran of m.w. about 40,000.

At the end of a storage period of about 54 weeks=at 8 deg. C. certain specimens made according to this example had a titre in pfu/ml (of original liquid volume before lyophilisation) within 0.5 of a log of the titre found immediately after lyophilisation.

EXAMPLE 4

A lyophilised preparation of the genetically disabled HSV-2 of example 1 can be made as in the example 1 except that the liquid before lyophilisation comprises, besides virus: 2.5% dextran (m.w. about 11,000), 0.5% sodium glutamate, 2.5% sucrose, and 0.1M Tris buffer, preferably about pH 7.5.

In variants of this example the sodium glutamate can be omitted. This example is free from protein, other than any protein forming part of the active vaccine component.

At the end of a storage period of about 25 weeks=at 8 deg. C. certain specimens made according to this example had a titre in pfu/ml (of original liquid volume before lyophilisation) within 0.5 of a log of the titre found immediately after lyophilisation, and had a titre of the order of $10^5$ to $10^6$ pfu/ml relative to the liquid volume before lyophilization.

EXAMPLE 5

A lyophilised preparation of the genetically disabled HSV-2 of example 1 can be made as in example 1 except that the liquid before lyophilisation comprises, besides virus: 2.5% dextran (m.w. about 40,000), 0.5% sodium glutamate, 5% sucrose, and 0.05M Tris buffer preferably about pH 7.5.

This example is free from protein, other than any protein forming part of the active vaccine component.

At the end of a storage period of about 40 weeks=at 8 deg. C. certain specimens made according to this example had a titre in pfu/ml (of original liquid volume before lyophilisation) within 0.5 of a log of the titre found immediately after lyophilisation and had a titre of the order of 10$\hat{5}$ to 10$\hat{6}$ pfu/ml relative to the liquid volume before lyophilization.

EXAMPLE 6

A lyophilised preparation of the genetically disabled HSV-2 of example 1 can be made as in example 1 except that the liquid before lyophilisation comprises, besides virus: 2.5% dextran (m.w. about 40,000), 0.5% sodium glutamate, 2.5% sucrose, and 0.1 M Tris buffer preferably about pH 7.5.

In variants of this example the sodium glutamate can be omitted.

This example is free from protein, other than any protein forming part of the active vaccine component.

At the end of a storage period of about 40 weeks at 8=deg. C. certain specimens made according to this example had a titre in pfu/ml (of original liquid volume before lyophilisation) within 0.5 of a log of the titre found immediately after lyophilisation.

EXAMPLE 7

A lyophilised preparation of the genetically disabled HSV-2 of example 1 can be made as in example 1 except that the liquid before lyophilisation comprises, besides virus: 5% lactose, 2.5% sucrose, 1.8% D-sorbitol, 0.1% sodium glutamate, 2% vegetable peptone, and 0.05 M Tris buffer preferably at a pH about 7.5.

In a variant of this example the sodium glutamate can be omitted. This example is free from protein, other than any protein forming part of the active vaccine component.

At the end of a storage period of about 25 weeks at 8 deg. C. certain specimens made according to this example had a titre in pfu/ml (of original liquid volume before lyophilisation) within 0.5 of a log of the titre found immediately after lyophilisation.

EXAMPLE 8

A lyophilised preparation of the genetically disabled HSV-2 of example 1 can be made as in example 1 except that the liquid before lyophilisation comprises, besides virus: 5% lactose, 5% sucrose, 1.8% D-sorbitol, 2% vegetable peptone, and 0.1 M Tris buffer preferably at a pH about 7.5.

This example is free from protein, other than any protein forming part of the active vaccine component.

At the end of a storage period of about 25 weeks at 8 deg. C. certain specimens made according to this example, in which sodium glutamate is omitted and the gelatin hydrolysate is replaced by vegetable peptone, had a titre in pfu/ml (of original liquid volume before lyophilisation) within 0.5 of a log of the titre found immediately after lyophilisation.

Examples of compositions according to the invention can usefully be freeze-dried using standard methods well known in the art for lyophilising biological material.

For example, the following freeze drying process can be used in connection with compositions of the invention e.g.

according to the examples given above, and is described below and without intent to limit the scope of the invention.

A virus composition for lyophilization as described herein, is first frozen at minus 60 deg. C. for 2 hours, and then dried at reduced pressure of 100 Mtorr using a drying procedure as follows:

The temperature of the composition is progressively increased to −42 deg. C. over the course of an hour, and held at this temperature for a further 60 hours. The temperature is then raised to +5 deg. C. over the course of 5 hours, and held at that temperature for about a further 7 hours. Finally, the temperature is raised to +10 deg. C. over the course of an hour, and held at that temperature for about a further 7 hours.

An alternative and sometimes preferred drying procedure is as follows: The composition is first frozen by lowering its temperature to −40 deg. C. over the course of 1 hour, and maintaining it at this temperature for a further 2 hours. The composition can then be subjected to a step intended to encourage enlargement of ice crystals: the temperature is raised to −15 deg. C. over the course of about 45 min and is maintained at that temperature for a further 2 hours. The temperature can then be lowered to 40 deg. C. over the course of 25 min and the composition then dried at reduced pressure of 50 Mtorr using a drying procedure as follows: The temperature is held at 40 deg. C. for 2 hours, then raised to −15 deg. C. over the course of about 45 min, and held at this temperature for a further hour. The temperature can then be lowered to −35 deg. C. over the course of an hour, and held at this temperature for about a further 32 hours. Then the temperature can be raised to +5 deg. C. over the course of about 3 hours, and held at that temperature for a further 8 hours.

In a variant of this example, following freezing of the composition, the temperature can be raised to 0 deg. C. instead of to −15 deg. C.

The invention described herein is susceptible of modifications and variations that will be apparent to the reader of ordinary skill in the field. In particular, and without limitation, features of prior art processes and compositions for vaccine preparations, e.g. as mentioned in documents referenced above, can be applied within the scope of this invention, and the present disclosure extends to modifications and variations of the compositions and other aspects of the present invention, including combinations and subcombinations of the features mentioned or described herein and in the mentioned publications and appended claims, which are hereby incorporated by reference in their entirety for all purposes.

What is claimed is:

1. A stabilized dried pharmaceutical composition, which is dispersible in aqueous liquid for injection, and which comprises (i) infectious genetically disabled herpesvirus, (ii) a polysaccharide or polysaccharide derivative having a molecular weight from about 5000, to about 70,000, and/or a source of mixed amino acids of vegetable or bacterial origin, (iii) a buffer, and (iv) a monosaccharide, oligosaccharide, or sugar alcohol, thereby to stabilize said disabled herpesvirus in said preparation.

2. A composition according to claim 1, which contains at least one amino acid or amino acid salt, for example L-glutamate or L-aspartate.

3. A composition according to claim 1 which is free from animal protein.

4. A composition according to claim 3, which is free from non-herpesvirus protein.

5. A composition according to claim 1 which contains a disaccharide.

6. A composition according to claim 5 wherein the disaccharide is lactose, sucrose, or trehalose.

7. A composition according to claim 1 which contains a monosaccharide or a sugar alcohol.

8. A composition according to claim 1 which contains vegetable peptone.

9. A composition according to claim 1 which contains dextran with a molecular weight in the range from about 5000 to about 70,000.

10. The composition according to claim 1, wherein the polysaccharide or polysaccharide derivative has a molecular weight from about 11,000 to about 40,000.

11. An injectable pharmaceutical liquid preparation which has been prepared by dispersing a stabilized dried composition according to claim 1 in sterile liquid for injection.

12. A composition according to claim 1, which comprises (i) infectious genetically disabled herpesvirus, (ii) dextran, (iii) buffer, (iv) sodium glutamate, and (v) sucrose.

13. A composition according to claim 1, wherein the buffer is Tris or Phosphate buffer.

14. A method of administering a composition according to claim 1 to a subject to immunize said subject, wherein said method comprises dispersing said composition in a sterile liquid, followed by administering said liquid to said subject by injection.

15. A method of preparing a pharmaceutical composition, which comprises lyophilizing an aqueous liquid comprising (i) infectious genetically disabled herpesvirus, (ii) a polysaccharide or polysaccharide derivative having a molecular weight from about 5000 to about 70,000, and/or a source of mixed amino acids of vegetable or bacterial origin, (iii) a buffer, and (iv) a monosaccharide, oligosaccharide, or sugar alcohol.

16. The method of claim 15, wherein the polysaccharide or polysaccharide derivative has a molecular weight from about 11,000 to about 40,000.

17. A method according to claim 15, wherein said aqueous liquid comprises a disaccharide at a concentration from 2 to 12% w/v.

18. A method according to claim 15, wherein said aqueous liquid comprises vegetable peptone at a concentration in the range from about 1 to about 4% w/v.

19. A method according to claim 15, wherein said aqueous liquid comprises dextran at a concentration from 1 to 5% w/v.

* * * * *